United States Patent [19]

McEwen et al.

[11] 4,254,014
[45] Mar. 3, 1981

[54] POLYCARBONATE CONTAINING A BIS(CYCLIC PHOSPHITE) AS A THERMAL STABILIZER

[75] Inventors: Gerald K. McEwen; Lowell S. Thomas, both of Midland, Mich.

[73] Assignee: The Dow Chemical Company, Midland, Mich.

[21] Appl. No.: 69,960

[22] Filed: Aug. 27, 1979

[51] Int. Cl.³ .......................... C07F 9/15; C08K 5/52
[52] U.S. Cl. ...................... 260/45.7 PH; 260/45.8 R; 260/927 R; 525/2
[58] Field of Search ....... 260/45.8 R, 927 R, 45.7 PH

[56] References Cited

U.S. PATENT DOCUMENTS

| | | | |
|---|---|---|---|
| 2,952,701 | 9/1960 | McConnell et al. | 260/927 R |
| 3,231,531 | 1/1966 | Buckley et al. | 260/45.75 W |
| 3,283,037 | 11/1966 | Davis | 260/927 R |
| 3,305,520 | 2/1967 | Fritz et al. | 260/45.7 PH |
| 3,467,733 | 9/1969 | Dever et al. | 260/927 R |
| 3,509,091 | 4/1970 | Cleveland et al. | 260/45.8 R |
| 3,970,635 | 7/1976 | Lawton et al. | 260/927 R |
| 4,066,611 | 1/1978 | Axelrod | 260/927 R |
| 4,088,709 | 5/1978 | Seymour et al. | 260/45.7 PH |

FOREIGN PATENT DOCUMENTS 810069  3/1959  United Kingdom .

*Primary Examiner*—Howard E. Schain
*Assistant Examiner*—R. A. White

[57] ABSTRACT

A polycarbonate such as a bisphenol-A homopolycarbonate containing a small amount of an aromatic bis(cyclic phosphite) such as 2,2'-[-(1-methylethylidene)-bis(4,1-phenyleneoxy-2,1-ethanediyloxy)]bis(5,5-dimethyl-1,3,2-dioxaphosphorinane) exhibits improved processability and thermal stability.

5 Claims, No Drawings

POLYCARBONATE CONTAINING A BIS(CYCLIC PHOSPHITE) AS A THERMAL STABILIZER

DESCRIPTION OF THE INVENTION

This invention relates to polycarbonates containing additives which increase the processability and thermal stability thereof.

Polycarbonates derived from reactions of dihydroxy-organic compounds, particularly the dihydric phenols, and carbonic acid derivatives such as phosgene have found extensive commercial application because of their excellent physical properties. These thermoplastic polymers appear to be particularly suitable for the manufacture of molded parts wherein impact strength, rigidity, toughness, heat resistance and excellent electrical properties are required.

Unfortunately, however, the polycarbonates are often difficult to mold or extrude into parts or articles. When these polymers are extruded or molded under hot melt conditions, they are difficult to process and are degraded, i.e., they yellow and lose some physical strength. Accordingly, it has become a practice to incorporate plasticizers to improve the processability, i.e., the extrudability or moldability of the polycarbonates. The incorporation of such plasticizers into the polycarbonate often deleteriously affects the physical properties of the polycarbonate.

In view of the deficiencies of many of the conventional polycarbonate compositions, it would be highly desirable to provide a polycarbonate composition having improved processability and thermal stability without adversely affecting other physical properties of the polycarbonate such as tensile and impact strength.

SUMMARY OF THE INVENTION

In one aspect, the present invention is a polycarbonate composition comprising a carbonate polymer having dispersed therein an aromatic bis(dioxaphosphorinane) in an amount sufficient to measurably increase the processability and/or the thermal stability of the carbonate polymer. Hereinafter, such composition shall be referred to as a stabilized polycarbonate. The stabilized polycarbonate of the present invention exhibits surprising processability, e.g., good melt flowability, and thermal stability, i.e., resists discoloration and weight loss upon exposure to high temperatures.

In another aspect, the present invention is an aromatic bis(dioxaphosphorinane) which is useful as a thermal stabilizer and/or processability aid in polycarbonates.

The stabilized polycarbonate of the present invention is suitably employed in most applications which polycarbonates have been previously utilized. Applications of particular interest for the utilization of the stabilized polycarbonates of this invention are as follows: automobile parts, e.g., air filters, fan housings, exterior components; housings for electrical motors, appliances, business and office equipment, and photographic equipment, lighting and aircraft applications.

DETAILED DESCRIPTION OF THE EMBODIMENTS

The polycarbonates employed in the present invention are advantageously aromatic carbonate polymers such as the trityl diol carbonates described in U.S. Pat. Nos. 3,036,036; 3,036,037; 3,036,038 and 3,036,039; polycarbonates of bis(ar-hydroxyphenyl)alkylidenes (often called bisphenol-A type diols) including their aromatically and aliphatically substituted derivatives such as disclosed in U.S. Pat. Nos. 2,999,835; 3,038,365 and 3,334,154; and carbonate polymers derived from other aromatic diols such as described in U.S. Pat. No. 3,169,121.

It is understood, of course, that the polycarbonate may be derived from (1) two or more different dihydric phenols or (2) a dihydric phenol and a glycol or a hydroxy- or acid-terminated polyester or a dibasic acid in the event a carbonate copolymer or interpolymer rather than a homopolymer is desired. Also suitable for the practice of this invention are blends of any one of the above carbonate polymers. Also included in the term "carbonate polymer" are the ester/carbonate copolymers of the types described in U.S. Pat. Nos. 3,169,121 and 4,105,633. Of the aforementioned carbonate polymers, the polycarbonates of bisphenol-A and derivatives, including copolycarbonates of bisphenol-A, are preferred. Methods for preparing carbonate polymers for use in the practice of this invention are well known, for example, several suitable methods are disclosed in the aforementioned patents which are hereby incorporated by reference in their entirety.

The aromatic bis(dioxaphosphorinane) of the present invention is advantageously represented by the formula:

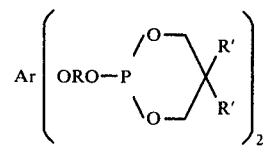

wherein Ar is a divalent aromatic radical having each of its valences (valence bonds) on an aromatic ring; each R is individually a divalent aliphatic radical and each R' is individually hydrogen or a monovalent organic radical provided that the aromatic bis(dioxaphosphorinane) is inert to the polycarbonate under conditions of fabrication and use. Exemplary Ar includes phenylene or aromatically substituted phenylene wherein the substituent(s) is halo, alkyl, aryl, amino, etc.; bis(phenylene)alkanes such as 2,2-bis(4-phenylene)propane and halogenated 2,2-bis(4-phenylene)propane such as 2,2-bis(ar,ar-dibromo-4-phenylene)propane; bis(phenylene)oxides and bis(phenylene)sulfides; and the like, with the bis(phenylene)alkanes, especially 2,2-bis(4-phenylene)propane (derived from bisphenol-A), being preferred. Exemplary R includes alkylene, e.g., ethylene and propylene; alkyleneoxyalkylene, alkylenethioalkylene, poly(alkyleneoxy)alkylene, poly(alkylenethio)alkylene, arylene and the like, with alkylene, especially ethylene, being preferred. Exemplary R' includes hydrogen, alkyl, and haloalkyl, with alkyl, especially methyl, being preferred.

Examples of preferred aromatic bis(dioxaphosphorinanes) include 2,2'-[-(1-methylethylidene)bis(4,1-phenyleneoxy-2,1-ethanediyloxy)]bis(5,5-dimethyl-1,3,2-dioxaphosphorinane).

The aromatic bis(dioxaphosphorinanes) employed in the practice of the present invention are readily prepared by reacting a halo(dioxaphosphorinane) of the formula:

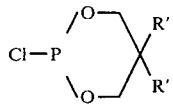

with a diol of the formula:

HOROArOROH in the presence of an amine catalyst such as triethylamine or similar trialkyl amine. The halo(dioxaphosphorinane) is advantageously produced by reacting phosphorus trichloride with pentaerylthritol or similar suitable diol. See, for example, the procedure described by R. S. Edmundson, Chem. Ind. (London) 27, 1220 (1965).

The stabilized polycarbonate of the present invention is suitably prepared by combining the carbonate polymer with an effective amount of aromatic bis(dioxaphosphorinane) (stabilizer) using any one of a variety of blending procedures conventionally employed for incorporating additives into carbonate polymer resins. For example, dry particulates of the carbonate polymer and the stabilizer may be dry blended and the resulting dry blend extruded into the desired shape.

While any amount of stabilizer that imparts to the polycarbonate an improved processability and/or an improved resistance to degradation upon exposure to heat is suitable, preferred amounts of the stabilizer are in the range from about 0.05 to about 1, especially from about 0.15 to about 0.25, weight percent based on the weight of the carbonate polymer.

In addition to the aforementioned aromatic bis(dioxaphosphorinane), other additives may be included in the stabilized polycarbonate of the present invention such as fillers, pigments, dyes, antioxidants, stabilizers, ultraviolet light absorbers, mold release agents and other additives commonly employed in polycarbonate resin formulations.

The following examples are given to further illustrate the invention and should not be construed as limiting its scope. In the following examples, all parts and percentages are by weight unless otherwise indicated.

EXAMPLE 1

Preparation of
2,2′-[(1-methylethylidene)bis(4,1-phenyleneoxy-2,1-ethanediyloxy)]bis(5,5-dimethyl-1,3,2-dioxaphosphorinane) (BPA-bicyclic phosphite)

To a 2-liter, 3-necked round bottom flask equipped with stirrer, nitrogen purge and addition funnel is added 137.5 g (1 mole) of PCl₃ dispersed in 100 ml of methylene chloride. A solution of 104 g (1 mole) of neopentylglycol [(CH₃)₂C(CH₂OH)₂] in 250 ml of methylene chloride is then added dropwise to the flask over a period of one hour. The reaction mixture is stirred for an additional 1.5 hours at 25° C. The reaction mixture contains 1-chloro-5,5-dimethyl-1,3,2-dioxaphosphorinane, i.e.,

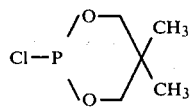

This product is transferred to the addition funnel and the flask is charged with 158 g (0.5 mole) of the diethylene glycol adduct of bisphenol-A,

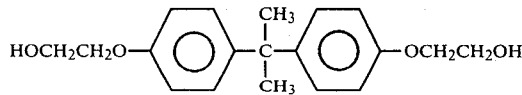

suspended in 250 ml of methylene chloride and 101 g (1 mole) of triethylamine. The stirred suspension is cooled to −10° C. and the chlorocyclic phosphorinane is added dropwise to the suspension. After the addition is complete, the flask is heated to room temperature and stirred for three hours. The reaction product is filtered to remove triethylamine hydrochloride and then stripped of solvent on a rotary evaporator. The desired BPA-bicyclic phosphite, represented by the formula:

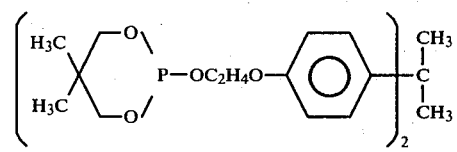

is recovered as a viscous liquid in a yield of 266 g.

PREPARATION OF STABILIZED POLYCARBONATE

A 8.17-g portion of the BPA-bicyclic phosphite is uniformly dispersed in 453 g of granular homopolycarbonate of bisphenol-A having a weight average molecular weight (Mw) of about 29,000 using a conventional household mixer. The resulting concentrate is then combined with additional homopolycarbonate to make about 4.1 Kg of stabilized polycarbonate by tumble blending the concentrate and homopolycarbonate for six hours. The resultant blend is dried at 120° C. overnight and extruded and chopped into pellets. The extruded pellets are tested for melt flow characteristics (processability) and then injection molded into test tabs and tested for thermal resistance. The results are reported in Table I.

For purposes of comparison, a similar polycarbonate blend is prepared using 2,2′-(1,2-ethanediylbis(oxy-2,1-ethanediyloxy))bis(5,5-dimethyl-1,3,2-dioxaphosphorinane) (EO-bicyclic phosphite) represented by the structural formula:

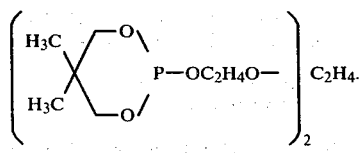

instead of the BP-bicyclic phosphite as a thermal stabilizer. Test tabs are similarly prepared from the blend and tested. The results are reported in Table I.

TABLE I

| Sample No. | Thermal Stabilizer (1) Type | Thermal Stabilizer (1) Amount, wt % | ΔMFV (2) decig/min # of Extrusions | ΔY (3) # of Extrusions | % MVR (4) 275° C. | % MVR (4) 300° C. | % MVR (4) 325° C. |
|---|---|---|---|---|---|---|---|
| 1 | BPA | 0.2 | 0.73/0<br>3:98/2<br>3.83/6 | −0.29/0<br>6.60/2<br>5.43/6 | 56 | 73 | 82 |
| A* | EO | 0.2 | 2.55/0<br>2.81/2<br>2.76/6 | 0.72/0<br>1.33/2<br>3.08/6 | 47 | 58 | 64 |

*Not an example of the invention.
(1) BPA - BPA-bicyclic phosphite EO - EO-bicyclic phosphite wt % - weight percent based on weight of polycarbonate.
(2) ASTM D-1238 (Condition O) wherein ΔMFV is the difference in the melt flow viscosities of the polycarbonate containing the stabilizer and the same polycarbonate containing none of the stabilizer.
(3) ASTM D-1925 wherein ΔY is the difference in yellowness index of the polycarbonate containing the stabilizer and the yellowness index of the same polycarbonate containing none of the stabilizer (control sample). A minus ΔY indicates that the yellowness index of the stabilized sample is less than that of the control sample.
(4) % MVR - percent melt viscosity reduction. Melt viscosity of stabilized polycarbonate is determined in poises at shear rate of 100 sec$^{-}$ using Mendelson's procedure described in Computer Programs for Plastics Engineers, edited by Klein, I., et al., Reinhold Book Corp., Sec. III pp. 124-131 (1968). % Reduction of melt viscosity is obtained by the following formula:

$$\% \text{ MVR} = \frac{\text{(melt viscosity of stabilized polycarbonate)} - \text{(melt viscosity of unstabilized polycarbonate)}}{\text{(melt viscosity of unstabilized polycarbonate)}} \times 100$$

As evidenced by the data shown in Table I, the BPA-bicyclic phosphite of the present invention gives substantially greater improvement of thermal stability and processability after several extrusions than does the EO-bicyclic phosphite.

What is claimed is:

1. An aromatic bis(dioxaphosphorinane) represented by the formula:

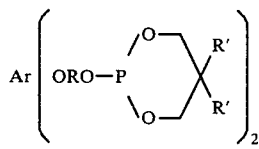

wherein Ar is a divalent aromatic radical having each of its valences on an aromatic ring; each R is individually a divalent aliphatic radical and each R' is individually hydrogen or a monovalent organic radical provided that the aromatic bis(dioxaphosphorinane) is inert to polycarbonates.

2. The bis(dioxaphosphorinane) of claim 1 which is 2,2'-[(1-methylethylidene)bis(4,1-phenyleneoxy-2,1-ethanediyloxy)]bis(5,5-dimethyl-1,3,2-dioxaphosphorinane.

3. A polycarbonate composition comprising a carbonate polymer having dispersed therein the aromatic bis(dioxaphosphorinane) of claim 1 in an amount sufficient to measurably increase the thermal stability or processability of the carbonate polymer.

4. The composition of claim 3 wherein the amount is in the range from about 0.05 to 1 weight percent of bis(dioxaphosphorinane) based on the weight of the carbonate polymer.

5. The composition of claims 3 or 4 wherein the bis(dioxaphosphorinane) is as defined in claim 2 and the carbonate polymer is a homopolycarbonate of bisphenol-A.

* * * * *